United States Patent [19]
Archibald et al.

[11] 3,969,528
[45] July 13, 1976

[54] HEXAHYDROIMIDAZO[1,5-A]PYRIDINES

[75] Inventors: John Leheup Archibald; Alan Chapman White, both of Windsor; Robin Michael Black, Porton, all of England

[73] Assignee: John Wyeth & Brother Limited, Maidenhead, England

[22] Filed: Apr. 8, 1975

[21] Appl. No.: 566,632

[30] Foreign Application Priority Data
Apr. 19, 1974 United Kingdom............... 17220/74

[52] U.S. Cl............................. 424/267; 260/293.55
[51] Int. Cl.²..................................... C07D 471/00
[58] Field of Search................ 260/293.55; 424/267

[56] References Cited
OTHER PUBLICATIONS
Bachman, et al. JACS 69:2022 (1947).
Jones, JACS 69:2346 (1947).

*Primary Examiner*—Henry R. Jiles
*Assistant Examiner*—C. M. S. Jaisle
*Attorney, Agent, or Firm*—Richard K. Jackson

[57] ABSTRACT

The invention relates to bases of the formula

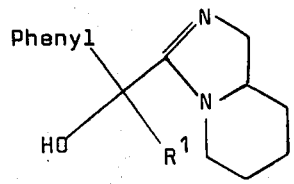

and their acid addition salts with pharmaceutically acceptable acids. In the formula $R^1$ represents phenyl or phenyl substituted by one or more hydroxyl, lower alkyl lower alkoxy, trifluoromethyl or halogen groups. The compounds have hypoglycemic activity.

4 Claims, No Drawings

HEXAHYDROIMIDAZO[1,5-a]PYRIDINES

This invention relates to heterocyclic compounds and more particularly to derivatives of hexahydroamidazo[1,5-a]pyridines, to process for preparing these compounds and to pharmaceutical preparations containing them.

The componds of the present invention are those of the general formula (I)

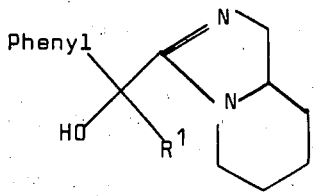
(I)

and their acid addition salts with pharmaceutically acceptable acids, wherein $R^1$ represents phenyl or phenyl substituted by one or more hydroxyl, lower alkyl, lower alkoxy, trifluoromethyl or halogen groups.

Since the compounds of the invention possess asymmetric carbon atoms, optical enantiomorphs are possible and the compounds of the invention may be in the form of pure enantiomorphs or mixtures of such enantiomorphs, such as racemates.

The term "lower" as used herein means that the radical referred to contains up to 6 carbon atoms. The radicals preferably contain up to 4 carbon atoms.

The group $R^1$ is an optionally substituted phenyl group in which the optional substituents are hydroxy, halogen (for example fluorine, chlorine or bromine), lower alkyl (for example methyl, ethyl, propyl or butyl), lower alkoxy (for example methoxy, ethoxy, propoxy or butoxy), or trifluoromethyl. Preferably $R^1$ represents phenyl or phenyl monosubstituted with halogen.

A preferred compound of general formula (I) is 1,5,6,7,8,8a-hexahydro-α,α-diphenylimidazo[1,5-a]-pyridine-3-methanol.

The compounds of the invention can be prepared by a process in which a ketone of general formula (II)

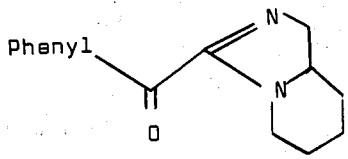
(II)

is reacted with an organometallic compound and if desired a free base is converted into an acid addition salt. The organometallic compound converts a ketone function to a group

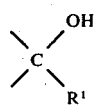

(where $R^1$ is as defined above). Suitable organometallic compounds include Grignard reagents of the general formula $R^1MgX$ (where $R^1$ is as defined above and X is halogen) and alkali metal compounds such as lithium derivatives of formula $R^1Li$ (where $R^1$ is as defined above) e.g. phenyl lithium. Preferably a Grignard reagent is used. The reaction with the organometallic compound is generally carried out in an inert organic solvent, for example ether or tetrahydrofuran.

The compound of general formula (II), may be prepared by the oxidation of 1,5,6,7,8,8a-hexahydro-α-phenyl-imidazo[1,5-a]pyridine-3-methanol. Preferably the oxidation is carried out with a mild oxidising agent such as manganese dioxide (for example in an inert organic solvent, e.g. dichloromethane, chloroform, benzene, acetone or aqueous acetone). The 1,5,6,7,8,8a-Hexahydro-α-phenyl-imidazo[1,5-a]pyridine-3-methanol starting material may be prepared by reacting 2-aminomethylpiperidine with an alkyl imidate of general formula (III)

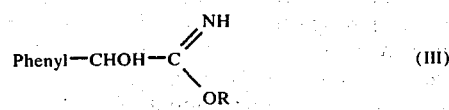
(III)

(where R is a lower alkyl group) or an acid addition salt thereof or with an amidine of formula (IV)

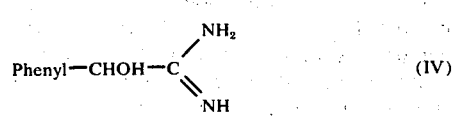
(IV)

or an acid addition salt thereof. Preferably the 2-aminomethylpiperidine is reacted with an alkyl mandelimidate, e.g. ethyl mandelimidate hydrochloride. The reaction can be carried out in an inert organic solvent, e.g. methanol or ethanol.

The bases of formula (I) are capable of forming acid addition salts with acids and the invention also provides the pharmaceutically acceptable salts of the bases. The salts may be isolated directly from the processes described above or prepared by dissolving the specific compound of formula (I) as its base in a suitable organic solvent, and treating it with a solution of the selected acid, methanesulphonic accordance with conventional procedures for preparing acid addition salts from base compounds generally. As examples of acids, there may be used any of hydrochloric, hydrobromic, tartaric, phosphoric, maleic, citric, methanesulfphonic and p-toluenesulphonic acids.

The optical isomers of the compounds of formula (I) may be prepared by resolving a racemic mixture by standard methods described in the literature.

The compounds of the invention are useful as hypoglycaemic agents.

The compounds are tested for hypoglycaemic activity by the following procedure:

Male rats weighing 170–200 grams are fasted overnight. A control blood sample is taken from the tail and the sample of test compound is then administered by stomach tube. Subsequent blood samples are taken at hourly intervals and the change in blood sugar concentration is determined. Representative of the compounds in this procedure 1,5,6,7,8,8a-hexahydro-α,α-diphenylimidazo[1,5-a]pyridine-3-methanol was found to produce a depression in blood sugar concentration of more than 30% for three of the hourly test samples when administered at 50 mg/kg.

As the compounds show pharmaceutical activity the invention further provides a pharmaceutical composition which comprises a compound of general formula (I) or a pharmaceutically acceptable salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from 5 mg. to 500 mg. or more, according to the particular need and the activity of the active ingredient. The invention also includes the compounds in the absence of carrier where the compounds are in unit dosage form. The daily dose of compound will vary depending upon the route of administration the particular compound employed and the particular animal involved. The daily dosage for humans could be, for example, within the range 50 to 1000 mg. depending upon the method of administration, the specific compound and the severity of the disease.

The following Examples illustrate the invention.

EXAMPLE 1

1,5,6,7,8,8a-Hexahydro-α-phenyimidazo[1,5-a]pyridine-3-methanol

To a stirred suspension of ethyl mandelimidate hydrochloride (40.6g.) in absolute ethanol (400 ml.) at 0°C was added 2-aminomethylpiperidine (Arch. Pharm., 1960, 293, 203–210; 21.43g.) in absolute ethanol (100 ml.). The mixture was warmed to room temperature and stirred for 30 minutes, refluxed for 6 hours and then allowed to cool to room temperature. The ethanol was evaporated off, and the residue diluted with water, acidified to pH 2 with hydrochloric acid, washed with chloroform, basified with ammonia and extracted into chloroform. The chloroform extracts were dried over magnesium sulphate and evaporated to an oil, which was dissolved in acetone. Ethereal HCl was added and the resulting precipitate washed with ether, crystallised from iso-propyl alcohol and re-crystallised from ethanol to give the title compound as the hydrochloride (15.0g), m.p. 130° to 132°C.

Analysis: Found C,59.26; H, 7.47; N,9.84 $C_{14}H_{18}N_2O.HCl.H_2O$; requires C,59.04; H, 7.43; N, 9.84%.

EXAMPLE 2

(1,5,6,7,8,8a-Hexahydroimidazo[1,5-a]pyridine-3-yl)phenyl ketone

The hydrochloride (4.63g.) from Example 1 was converted into the free base by dissolving it in water, adding ammonia solution and extracting into chloroform. The chloroform extracts were dried and evaporated. The resulting material was dissolved in dichloromethane (250 ml.) and 'activated' manganese dioxide (25g.) was added. The mixture was stirred for 5 hours, then the manganese dioxide was removed by filtration and the dichloromethane evaporated off to leave 3.05g of the title compound as an oil.

EXAMPLE 3

1,5,6,7,8,8a-Hexahydro-α,α-diphenylimidazo[1,5-a]pyridine-3-methanol

The oil from Example 2 was dissolved in dried ether (25 ml.) and immediately added to phenylmagnesium bromide (prepared from 1.23g. magnesium and 8.00g. bromobenzene) in 150ml. dried ether. The mixture was stirred at room temperature for 16 hours. It was then poured on to a mixture of ammonium chloride (2.7g.) and ice and basified with ammonium solution. The solid remaining in the mixture was removed by filtration, and the ether layer was combined with chloroform extracts of the aqueous layer, dried over magnesium sulphate and evaporated to a residue. This residue and that from chloroform washings of the solid remaining after the Grignard reaction was crystallised from ethanol to give the title compound (0.56g.), m.p. 131°–3°C.

Analysis: Found C, 78.26; H, 7.17; N, 9.00 $C_{20}H_{22}N_2O$; requires C, 78.40; H, 7.24; N, 9.14%.

In an analogous manner, reaction of the ketone of Example 2 with m-chlorophenylmagnesium bromide and p-chlorophenylmagnesium bromide gives respectively α-(m-chlorophenyl)-α-phenyl-1,5,6,7,8,8a-hexahydroimidazo[1,5-a]pyridine-3-methanol and α-(p-chlorophenyl)-α-phenyl-1,5,6,7,8,8a-hexahydroimidazo[1,5-a]pyridine 3-methanol. Similarly, reaction of the ketone of Example 2 with p-methoxyphenylmagnesium bromide and o-methylphenylmagnesium bromide gives respectively α-(p-methoxyphenyl)-α-phenyl-1,5,6,7,8,8a-hexahydroimidazo[1,5-a]pyridine-3-methanol and α-(o-methylphenyl)-α-phenyl-1,5,6,7,8,8a-hexahydroimidazo[1,5-a]pyridine-3-methanol.

What is claimed is:

1. A compound selected from the group consisting of bases having the formula (I)

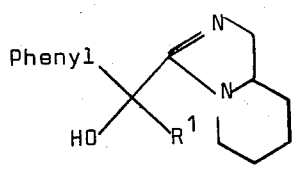

(I)

and the acid addition salts of said bases with pharmaceutically acceptable acids, wherein $R^1$ represents phenyl or phenyl substituted by one or more hydroxyl, lower alkyl, lower alkoxy, trifluoromethyl or halogen groups.

2. A compound according to claim 1 wherein $R^1$ represents phenyl or phenyl monosubstituted with halogen.

3. A compound according to claim 1 which is 1,5,6,7,8,8a-hexahydro-α,α-diphenylimidazo[1,5-a]pyridine-3-methanol.

4. A hypoglycaemic composition comprising a hypoglycaemically effective amount of a compound selected from the group consisting of bases having the formula (I)

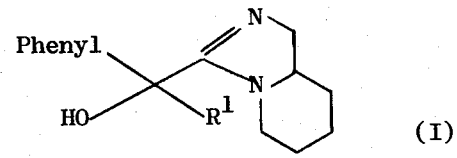

(I)

and the acid addition salts of said bases with pharmaceutically acceptable acids, wherein $R^1$ represents phenyl or phenyl substituted by one or more hydroxyl, lower alkyl, lower alkoxy, trifluoromethyl or halogen groups, in association with a pharmaceutically acceptable carrier.

* * * * *